(12) United States Patent
Sokolowski et al.

(10) Patent No.: US 7,354,491 B2
(45) Date of Patent: *Apr. 8, 2008

(54) METHOD AND APPARATUS FOR UNIVERSAL METALLURGICAL SIMULATION AND ANALYSIS

(76) Inventors: Jerzy H. Sokolowski, 3683 Inglewood Avenue, Windsor, Ontario (CA) N9E 4P3; Witold T. Kierkus, 5800 Cabot Avenue, La Salle, Ontario (CA) N9H 1M1; Marcin Stanislaw Kasprzak, Wschodnia 1 No. 24, Ruda Slaska 7 (PL) 41707; Wojciech Jan Kasprzak, 154 Campbell Avenue, Windsor, Ontario (CA) N9B 2H2

( * ) Notice: Subject to any disclaimer, the term of this patent is extended or adjusted under 35 U.S.C. 154(b) by 651 days.

This patent is subject to a terminal disclaimer.

(21) Appl. No.: 10/498,239

(22) PCT Filed: Dec. 12, 2002

(86) PCT No.: PCT/CA02/01903

§ 371 (c)(1),
(2), (4) Date: Jun. 10, 2004

(87) PCT Pub. No.: WO03/054533

PCT Pub. Date: Jul. 3, 2003

(65) Prior Publication Data

US 2005/0151306 A1 Jul. 14, 2005

(51) Int. Cl.
*C21D 11/00* (2006.01)
(52) U.S. Cl. .......................... 148/508; 266/80; 266/87
(58) Field of Classification Search ............... 266/80, 266/87, 44; 148/508
See application file for complete search history.

(56) References Cited

U.S. PATENT DOCUMENTS 3,377,838 A * 4/1968 Kanazawa et al. ............ 374/56

(Continued)

FOREIGN PATENT DOCUMENTS

DE 4411242 A1 * 10/1995

OTHER PUBLICATIONS

Dahake, "Precision Induction Heating With Advanced Solid State Technology", *Ameritherm Inc.*, www.ameritherm.com, pp. 1-7, no date.

(Continued)

*Primary Examiner*—Scott Kastler
(74) *Attorney, Agent, or Firm*—Dennis R. Haszko

(57) ABSTRACT

A method and apparatus (5) for simulating and analyzing industrial thermal processes, including industrial heat-treatment, processes, melting, solidification, quenching and the like, used in the manufacture of metals, alloys and metal matrix composite components. The apparatus (5) includes an optional environmental chamber (10) used for situations where testing room conditions are too hot or too cold and would thus interfere with operation of the apparatus (5) without such chamber (10). The apparatus (5) includes a multifunctional excitation coil (40) that serves the function of the omitted environmental chamber (10). The apparatus (5) also includes one or more high frequency resonant inverters (15) and a cooling means (20). The apparatus (5) integrates melting and thermal processing capabilities with a thermal analyzer and a control system. The apparatus (5) allows for the rapid design and optimization of industrial thermal processes used in the manufacture of metallurgical engineering material with superior structural and metallurgical chactacterics, suitable for advanced component service performance.

29 Claims, 3 Drawing Sheets

U.S. PATENT DOCUMENTS

| | | |
|---|---|---|
| 5,922,147 A | 7/1999 | Valtierra-Gallardo et al. |
| 6,224,693 B1 | 5/2001 | Garza-Ondarza et al. |
| 7,255,828 B2 * | 8/2007 | Kasprzak et al. ............ 266/87 |

OTHER PUBLICATIONS

"RF Power Supplies For Precision Induction Heating", *Ameritherm Inc.*, www.ameritherm.com, Dec. 1999.

"Induction Notes", *Ameritherm Inc.*, www.ameritherm.com, vol. 2, No. 1, pp. 1-12, no date.

Zinn et al., "Coil design and fabrication: basic design and modifications", *Heat Treating*, Jun. 1988, pp. 32-36.

Zinn et al., "Coil design and fabrication: part 2, specialty coils", *Heat Treating*, Aug. 1988, pp. 29-32.

Zinn et al., "Coil design and fabrication: part 3, fabrication principles", *Heat Treating*, Oct. 1988, pp. 39-41.

* cited by examiner

METHOD AND APPARATUS FOR UNIVERSAL METALLURGICAL SIMULATION AND ANALYSIS

BACKGROUND OF THE INVENTION

1. Field of the Invention

The present invention relates to a method and an apparatus for simulating and analyzing industrial processes in a laboratory environment or for use in a part of a mass production line of engineered components. More specifically, the present invention provides for a method and apparatus for simulating and analyzing temperature and time dependent industrial thermal processes in a laboratory setting with a high degree of accuracy and repeatability.

2. Description of the Prior Art

The manufacture of metals, alloys or metal matrix composite components is a complex process. It involves a variety of thermal, chemical, and physical mechanisms that influence the structural and mechanical properties of final products. The only effective way to design, analyze, and optimize new and existing industrial thermal processes is to develop a complete quantitative knowledge of and an understanding of the relationships between the process variables and the desired properties of the final products.

One of the fundamental elements in the understanding of the effects of these thermal processes is the examination of the key structural and mechanical properties of products, which were treated by thermal, thermo-physical, thermo-chemical or thermo-electromagnetic processes. Simulating and quantifying the effects of the various thermal process parameters on a resulting work piece structure and determined service characteristics can provide an accurate picture of every important aspect of the given thermal process as mentioned above, including an "energy signature" of the product. The information gained in the given metallurgical experiments can be used to design and optimize industrial thermal procedures that produce products with predefined engineering specifications.

Simulation of industrial thermal processes in a laboratory environment has traditionally been performed using separate melting, liquid metal treatments, heat treatment, and quenching equipment. In most situations, the process optimization is evaluated using the well known metallographic approach. The use of the thermal analysis technique for thermal process optimization is seldom used due to its analytical and experimental limitations (i.e., lack of necessary information for accurate quantitative analysis of metallurgical reactions, thermal hysterisis during the complex thermal processes, . . . etc.). Moreover, industrial and laboratory melting and heat treatment furnaces, including those which are electrical or gas powered are difficult to control and have restricted utility due to their large thermal capacitance and consequently large time constant (i.e., the time and temperature response of the tested work piece). Often there is a considerable difference in the temperature between the work piece and the furnace chamber itself, which can negatively affect the work piece characteristics (e.g., incipient melting). Consequently, it is extremely difficult to optimize quickly any new and sophisticated thermal processes using commercially available laboratory and industrial equipment.

Rapid optimization of new and sophisticated thermal processes is also hindered for other reasons such as the inability to conduct continuous or interrupted melt and work piece(s) heat treatment operations with on-line work piece metallurgical characterization. In addition, the transportation of the work piece, between testing stations, poses a safety hazard and, as well, a loss of continuity for the process itself and for the recorded data, elements vital for the assessment of the process parameters. Finally, because the sample is being moved from station to station, continuous on-line temperature measurement is impossible. Therefore, what occurs within the sample at key stages of the process may become lost in an analytical "black box". With traditional methods, only final metallurgical characteristics of the entire process can be obtained, rather than the ones developed during individual operations, which would be indispensable for the work piece itself and for thermal process optimization.

Furthermore, laboratory computer and experimental simulations of the industrial thermal processes have frequently been proven inadequate due to the lack of sufficiently high experimental precision; the inability to carry out experiments on sufficiently large test samples in order to perform further physical testing; and because the present day laboratory facilities, in most cases, are unable to replicate and fully control all relevant process variables that are characteristic for the production environment.

In order to satisfy the growing demand by industry for considerably improved products having predetermined performance characteristics, it is necessary to scientifically optimize heat treatment routines for fulfilling the requirements of specific applications. To date, such tasks were performed relying on experimental data from a Differential Scanning Calorimeter (DSC), Conventional Thermal Analysis (CTA) or Differential Thermal Analysis (DTA). However, the microscopic size of the DSC and DTA test samples and their restricted experimental conditions do not allow for metallurgical assessment of an actual industrial casting and the manufacturing process to which it is subjected (i.e., macro segregation, porosity and its distribution, grain size, . . . etc.).

In addition, transformation of laboratory settings to industrial scale production has been difficult as prior art laboratory experiments have not been adequately accurate and could not replicate the multitude of variables in an industrial environment. Advanced process optimization requires a laboratory system with testing, analytical capabilities, and control functions far exceeding those systems currently known in the art.

What is needed therefore is an apparatus that overcomes the difficulties of the prior art. More specifically, such an apparatus is needed that consolidates the capabilities of several instruments into a single apparatus which is easy and less expensive to set up, requires less floor space, has a less demanding maintenance schedule and is safer, by eliminating manual transfers of the test sample (i.e., work piece). Such an apparatus should perform thermal analysis by recording and analyzing the "energy signature" of a test sample with a high degree of accuracy and repeatability.

Still further, what is needed is that such an apparatus should simulate a variety of industrial melt and work piece (s) heat treatment processes and allows for the evaluation of physical properties of the material, such as specific heat, total heat or phase transformation (i.e., latent heat), or the heat of transformations of individual, identifiable reactions during phase transformations. Such an apparatus should be fully programmable and capable of a step change in power input heat source and a wide variety of cooling media, which guarantees the fastest temperature response of the test sample.

Moreover, such an apparatus should have the simulation capabilities and related test sample size, which allows for application of the simulation analysis results directly to full size components. This will reduce the cost and time required for "trial and error" experiments performed in an industrial environment.

SUMMARY OF THE INVENTION

The present invention includes a Universal Metallurgical Simulator and Analyzer (UMSA) apparatus for simulating and analyzing industrial processes, including a holder for a test sample equipped with a cooling means, a crucible, at least one heat source for varying the temperature of the test sample in cooperation with the crucible, at least one sensor, a data acquisition means for recording data collected by the at least one sensor during the industrial processes, a programmable controller for controlling at least one operating parameter of the industrial processes and for adjusting the at least one operating parameter based on the data collected by the data acquisition means, at least one multifunctional excitation coil having a heating-cooling mode and capable of delivering protective gas to surfaces of the test sample, wherein the holder is coupled to the heat source, the at least one sensor is connected to the test sample and the data acquisition means, and the controller is coupled to the heat source and the data acquisition means.

As well, the present invention includes a method for simulating and analyzing industrial processes using the UMSA apparatus, including: heating a test sample with a heat source; cooling the test sample; quenching the test sample; isothermally holding a the liquid, semi-solid, and solid test sample(s) at a predetermined temperature for a specified period of time; surrounding surfaces the test sample with protective gas to protect the test sample from degradation during operation of the UMS A apparatus; treating the test sample with protective media; monitoring and controlling temperature/time process parameters of the test sample during the heating, the cooling, and the isothermally holding steps; and analyzing physical characteristics of the test sample during and after completion of the industrial processes.

The present invention overcomes the difficulties of the prior art, as it uniquely consolidates the capabilities of several instruments into a single apparatus which is versatile, both easy and less expensive to set up, requires less floor space, requires a less demanding maintenance schedule, and is much safer than prior art methods and apparatus because the UMSA eliminates manual transfers of the test sample (i.e., work piece). The apparatus can perform thermal analysis by recording and analyzing the "energy signature" of a test sample with a high degree of accuracy and repeatability. The apparatus simulates a variety of industrial heat treatment processes and allows for the evaluation of physical properties of the material, such as specific heat, total heat or phase transformation (i.e., latent heat), or the heat of transformations of individual, identifiable reactions during phase transformations.

The UMSA apparatus is fully programmable and is capable of a step change in power input heat source and a wide variety of cooling media This virtually guarantees the fastest temperature response of the test sample.

Moreover, the UMSA apparatus includes the simulation capabilities and related test sample size that allows for application of the UMSA analysis results directly to full size components. This advantageously reduces the cost and time required for "trial and error" experiments performed in an industrial environment. Accordingly, cost-effective experimental trials in small samples of a given metallurgical material can very quickly occur with the related UMSA analysis thereafter providing important data for large-scale production using that metallurgical material.

The UMSA system is capable of varying, in a controlled manner, the desired thermal gradient(s) in the work piece(s), and therefore resulting micro and macrostructure, during its solidification, quenching or heat treatment processes, effectively changing the components' service performance. This control can be executed by the customized configuration (i.e., geometry) of the Multifunctional Excitation Coil(s) and the process environment. Furthermore, the thermal process cycle(s) can be superimposed on the other testing conditions (i.e., a simultaneously performed high cycle fatigue test) during work piece(s) evaluation.

The Universal Metallurgical Simulator and Analyzer (UMSA) is a state-of-the-art closed-loop research and manufacturing system that combines sophisticated melting and thermal processes and Advanced Thermal Analysis (ATA) capabilities. Such ATA methodology is discussed within and herein incorporated by reference to: W. T. Kierkus and J. H. Sokolowski, "*Recent Advances in CCA: A New Method of Determining "Baseline" Equation*", AFS Transactions, 1999, v. 107, 161-167 (ISBN 0-87433-200-1); M. B. Djurdjevic, W. Kasprzak, C. A. Kierkus, W. T. Kierkus and J. H. Sokolowski, "*Quantification of Cu Enriched Phases in Synthetic 3XX Aluminum Alloys Using the Thermal Analysis Technique, AFS Transactions*", 15th Casting Congress, Dallas, USA, 2001; and, M. B. Djurdjevic, R. Hasenbusch and J. H. Sokolowski, "*Assessment of the Hydrogen Level in the 319 Aluminum Alloy Melt using the Thermal Analysis Technique*", 131st TMS Annual Meeting, Seattle, Wash., USA, Feb. 17-21 2002. The UMSA's integral thermal analysis system can perform an in-situ, continuous assessment of macro test samples and/or of component structural and metallurgical characteristics with microscopic resolution.

The UMSA System Process Control program is capable of simulating various technological processes at near thermal equilibrium of the test sample (work piece), as well as at very rapid temperature change conditions (i.e., material quenching). The System's operating conditions can be controlled with a high degree of accuracy and precision This allows for the easy integration of the UMSA with other equipment, in order to vary the test sample (work piece) working environment characteristic parameters, such as: atmosphere (active or inert gas), pressure, stress, electromagnetic field, ultrasound and others. The UMSA system, therefore, allows for arbitrarily selected sequential processing of the test sample (work piece) through liquid, semi-solid and solid states in a predefined order. The Energy Signature output, from the test sample (work piece), created by the instrument's ATA algorithm, can then be compared and statistically evaluated by comparison with other experimental data stored in the System's database.

The capabilities of the UMSA system allow for rapid design and optimization of the composition of metals, metal alloys, metal matrix composites and their thermal processing, resulting in superior structural and metallurgical characteristics, suitable for advanced component service performance. This System also has the unique capability to rapidly create a database for the computer simulation of thermal processes. This database includes properties like: specific heat, latent heat of fusion, fraction solid, temperature of metallurgical reactions, . . . etc., for statistical correlation with subsequently quantified component metallurgical properties.

The preferred embodiment of the present invention will hereinafter be described in detail with reference to the accompanying drawing.

DETAILED DESCRIPTION OF THE INVENTION

Figure 1:
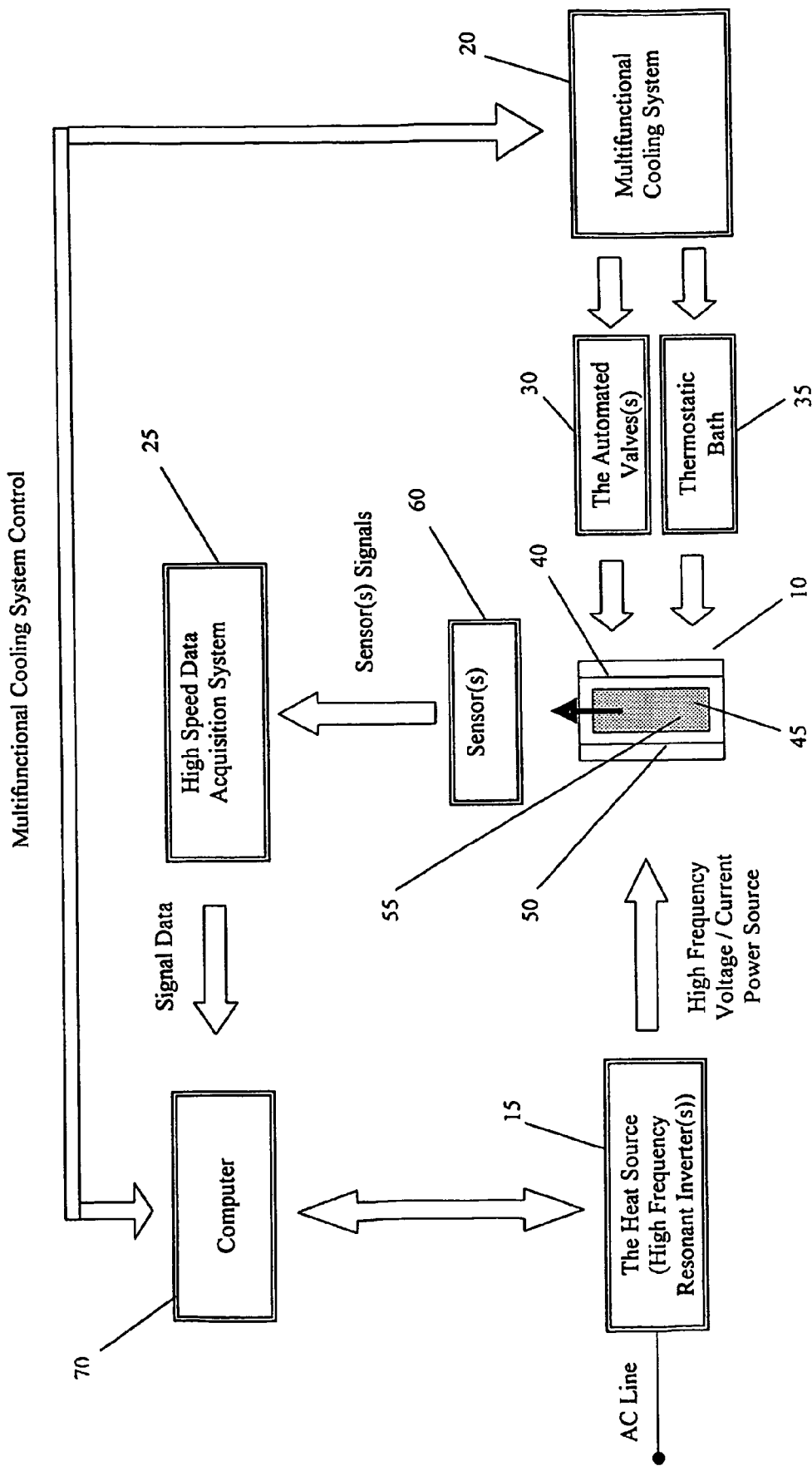
FIG. 1 is a block diagram view of the preferred embodiment of the present invention.

The invention will be described for the purposes of illustration only in connection with certain embodiments; however, it is to be understood that other objects and advantages of the present invention will be made apparent by the following description of the drawings according to the present invention. While a preferred embodiment is disclosed, this is not intended to be limiting. Rather, the general principles set forth herein are considered to be merely illustrative of the scope of the present invention and it is to be further understood that numerous changes may be made without straying from the scope of the present invention.

According to the preferred embodiment, the UMSA apparatus simulates and analyzes industrial thermal processes such as industrial heat-treatment processes, melting, solidification quenching . . . etc., in a laboratory environment including the ability to analyze the properties of a test sample at various stages of an industrial thermal process in order to determine the effects of the process on the properties of the test samples potentially with a high degree of accuracy and precision. The UMSA apparatus performs laboratory experiments, optimizations and simulations of industrial processes, as well as controlling a mass production line. The UMSA apparatus is readily used in a wide variety of industrial applications such as, but not limited to, the manufacturing, developing, and testing of light engineering materials including (Al, Mg, and Ti based alloys) that are essential for the automotive and aerospace industries. Moreover, the UMSA apparatus is useful in the development of new ferrous materials such as alloy steels and cast irons, specialty alloys, . . . etc. Furthermore, the design of energy efficient, continuous manufacturing of novel lightweight materials is assisted by the deployment of the UMSA apparatus, as it can precisely control and analyze crucial characteristics of "mushy zone" metallurgical reactions using sufficiently large test samples. Moreover, the UMSA apparatus can be used to direct liquid metal treatment, solidification, thermal sand removal, solution treatment, and artificial aging processes.

Among many other capabilities, the UMSA apparatus includes thermal options and flexibility of application, allows for performance of standard tests, in their present or modified form including the American Society for Testing and Materials (ASTM) Jorminy Test (i.e., evaluation of a material's hardening ability), evaluation of the aluminum alloys' grain size (Aluminum Company of Canada (ALCAN) or Aluminum Company of America (ALCOA) Tests), the tendency of the aluminum melt to hydrogen related porosity (Quantitative Reduced Pressure Test (QRPT) and/or the Re-melted Reduced Pressure Test (RRPT)). In addition the QRPT/RRPT apparatus can be instrumented with the UMSA Advanced Thermal Analysis (ATA) system for quantitative hydrogen and porosity analysis. Furthermore, the UMSA system can be utilized for controlled melting, solidification, and testing under a protective environment for the assessment of liquid metal cleanliness (i.e., evaluation of insoluble inclusion content using the Porous Disk Filtration Apparatus (PoDFA)).

The UMSA apparatus includes a heat source, a means for housing a test sample (work piece), at least one sensor and a programmable data acquisition and control means. The apparatus may further comprise a cooling means and an environmental chamber. In accordance with the present invention, the heat source can be selected from means that produce induction, electric resistance, or infrared radiation. It should be readily understood that any suitable heating means could be provided without straying from the intended scope of the present invention. In the preferred embodiment as illustrated, the heat source is one or more a High Frequency Resonant Inverters (HFRI) which supply a high frequency voltage/electric current to one or more water cooled Multifunctional Excitation Coils (MEC). The output power changes to maintain the required heating rate controlled by a Temperature Process Controller (TPC). The heat source operates above the human hearing threshold and provides high efficiency operation with a low level of electromagnetic interference and high dynamic output power control.

The invention also includes a housing means for holding the material sample (i.e., work piece) to be tested/analyzed. The housing means is includes at least one test sample crucible and a test sample holder. The crucible can be equipped with a riser (in this case the crucible consists of two parts joined together) to ensure the directional solidification conditions. The material of the crucible is dependant on the type of material to be processed. For instance, a crucible fabricated from non-magnetic steel would increase the eddy currents within the crucible whereas a ceramic crucible would increase the eddy currents and thus the heat within the test sample itself Optionally, the test sample holder that supports the crucible during testing and simulation dynamically moves, thereby adjusting the position of the test sample with respect to the heating means. Accordingly, it is possible to set the penetration depth to a minimum, for instance as needed, to avoid "unwanted" changes to the test sample. Furthermore, the test sample holder can be used to perform rapid quenching operations by dropping the test sample into the cooling medium. It should be understood that cooling is generally effectuated only on the visible surface of the test sample, while heating is generally effectuated throughout the test sample subject to any required penetration requirements as mentioned above. Temperature recording can continue during the quenching operation and the mechanical and structural properties of the test sample can be analyzed later.

The UMSA apparatus also contains sensors that are capable of measuring operating system parameters such as temperature, pressure, and flow. It should be readily understood that any type of sensor known to one skilled in the art are used for sensing purposes discussed herein without straying from the intended scope of the present invention. The sensors are connected to a high-speed data acquisition means, which records the sensor-generated signals and transmits the data to the control means. The control means is fully programmable and it can also be set to automatically duplicate time and temperature data files obtained from actual industrial processes. Any suitable control means may be used including, without limitation, a lat-top computer, a mainframe computer, or any similar microprocessor-based device (i.e., Central Processing Unit (CPU)). The high-speed data acquisition means is capable of recording multiple data inputs.

The analysis of the sensed data is performed by the Advanced Thermal Analysis (ATA) methodology (discussed in more detail below), which allows for precise quantification and statistical correlation of the structural, physical and chemical characteristic parameters of the material tested (e.g., specific heat, latent heat of fusion, temperatures of metallurgical reactions, fraction solid temperature function, . . . etc.). The results obtained from the ATA method are subsequently statistically correlated with the sample microstructure and mechanical properties. This information is used to generate fundamental scientific knowledge about melting and solidification processes. This information is also used to aid in design, for example, of industrial heat treatment procedures that produce materials with predefined engineering specifications.

As mentioned, the control means may be a laptop computer or some other form of CPU that is located adjacent or near the UMSA apparatus. Still further, it should be noted that software of the programmable control means is capable of performing, through a Local Area Network (LAN) or Internet connection, the programming, monitoring and controlling of the operating parameters of the testing procedure. Accordingly, the CPU may be either on-site or off-location. The parameters may either be entered by an operator or copied from the system memory, as a digitally duplicated, real industrial process file. The software also controls, in real-time or as a post-processing operation, the collection, analysis, and storage of the sensor signals received by the data acquisition means.

In a further embodiment of the invention, the cooling means can be applied to any surface or can be controlled internally. According to the preferred embodiment, the cooling means applied to the surface consists of at least one spiral pipe with several outlets that surrounds the test sample and a cooling medium, which is blown directly on the test sample surface. It should be understood that while a specific shape (i.e., spiral) is mentioned, any suitable shape is well within the scope of the present invention. Further, the cooling means is fully integrated with the MEC such that the MEC is made from at least two or more conductors. The first conductor has heating capabilities, the second would deliver the cooling medium to the surface(s) of the test sample through several outlets within the conductor, and a possible third or more would deliver an alternative medium such as, but not limited to, protective gases, water, air/water mists, or any suitable cooling media. For instance, rapid quenching operations may require a water/salt solution bath, a low temperature alloy, or any other suitable type of media. Controlling the power supplied to the cooling means, the flow rate and nature of the cooling medium regulates the cooling rate of the test sample. The cooling means is capable of controlled cooling of a MEC by circulating the cooling medium. This is preferably accomplished by using a thermostatic bath.

In a further embodiment of the invention, the apparatus includes an environmental chamber, which allows processing to be conducted under reduced or elevated pressure conditions, or under a chemically active or protective (i.e., inert) atmosphere. The chamber also allows for exposure of either selected or entire surfaces of the test sample to solid (i.e., powder) or liquid layers in order to protect the tested material from degradation of its properties.

In the preferred embodiment, the heat source is coupled with a highly accurate temperature process controller, such as an adaptable Proportional-Integral-Differential (PID) or a Proportional-Integral (PI) controller using fuzzy logic techniques. The temperature of the process can be controlled based on the signal received from one selected temperature sensor or on the averaged signal of several temperature sensors. The required heating and cooling (i.e., quenching) rates of the test sample can therefore be regulated with a great degree of flexibility.

Figure 2:
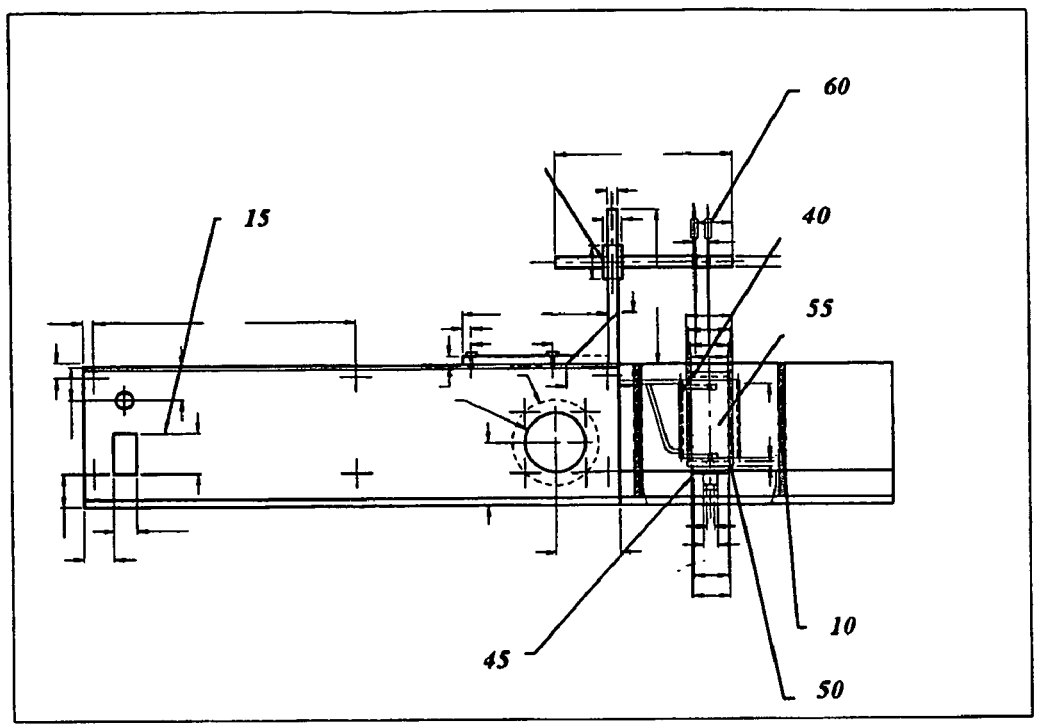
FIG. 2 is a schematic side view of the UMSA apparatus according to the preferred embodiment of the present invention.
Figure 3:
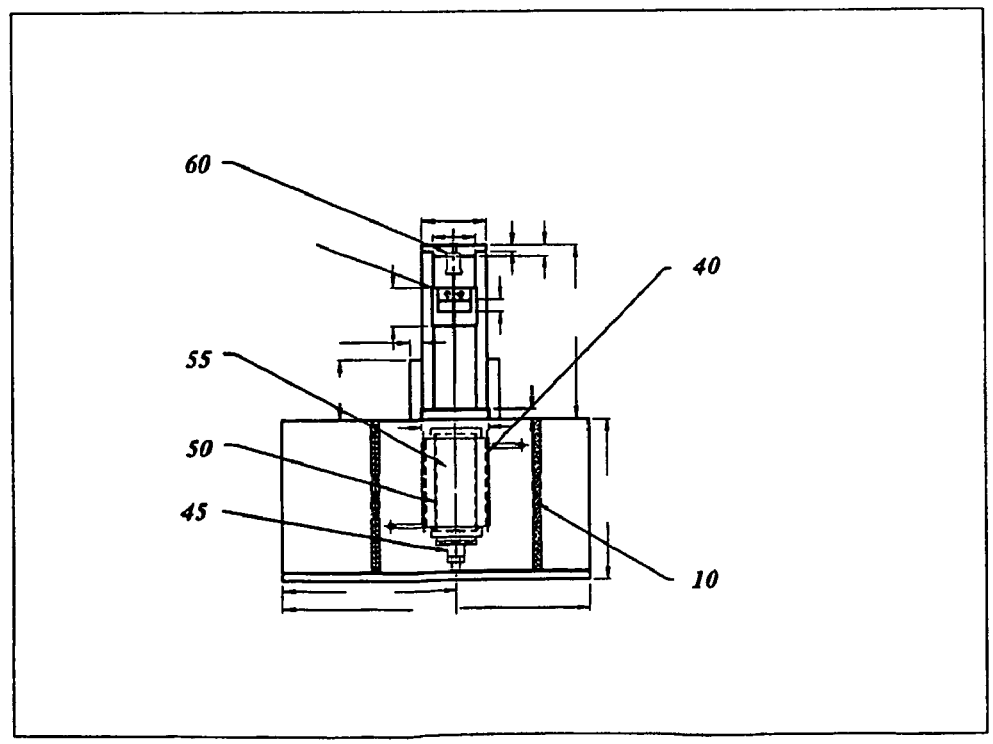
FIG. 3 is a schematic front view of the UMSA apparatus according to the preferred embodiment of the present invention.
Figure 4:
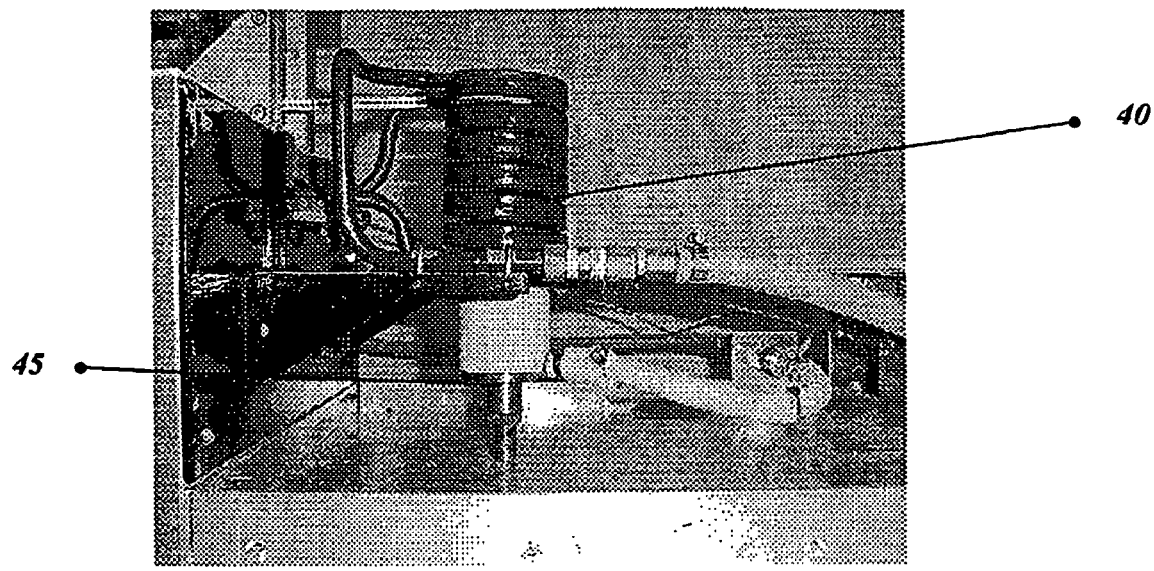
FIG. 4 is a perspective side view detailing the MEC of the UMSA apparatus according to the preferred embodiment of the present invention.
Figure 5:
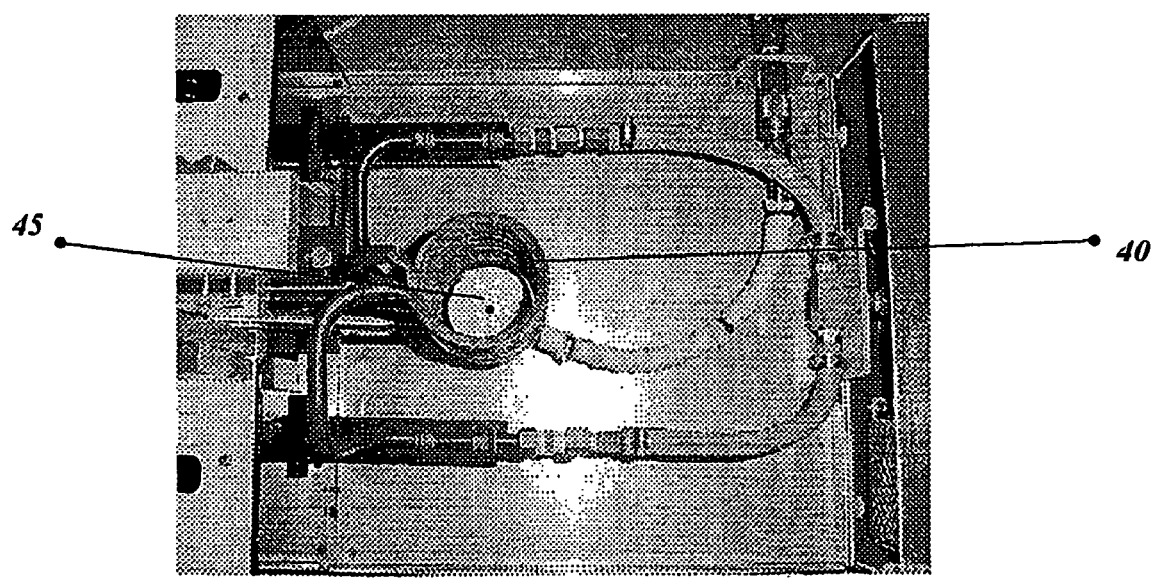
FIG. 5 is a perspective top view detailing the MEC of the UMSA apparatus according to the preferred embodiment of the present invention.

With reference to FIG. 1, there is illustrated a block diagram view according to the preferred embodiment of the present invention. Further, FIGS. 2 and 3 show schematics of the UMSA apparatus in side and front views and FIGS. 4 and 5 show details of the MEC within the UMSA apparatus. It should be readily understood that while a specific implementation and related configuration are shown, variations may occur in such configuration without straying from the intended scope of the present invention. Moreover, the FIGS. 2 though 5 are presented for clarity of illustrative purposes and should not be considered as limiting.

With further reference to the FIGS. 1-5, there is shown an UMSA apparatus 5 includes an environmental chamber 10. While the environmental chamber 10 is shown for illustrative purposes, it should be noted that the environmental chamber 10 is not necessary in all implementations of the present invention. Indeed, such a chamber may be required where testing room conditions where the UMSA apparatus is being used are too hot or too cold and would thus interfere with operation of the UMSA apparatus without such chamber. In such instances where testing room conditions are not extreme, the MEC 40 serves the function of the omitted environmental chamber 10. The environmental chamber is arranged with one or more HFRIs 15, a cooling means 20 as discussed in detail above, and a data acquisition means 25. As shown, the cooling means 20 includes two fluids coupled to the environmental chamber 10 through a valve means 30 and a thermostatic bath 35. The HFRI 15 is connected to the MEC 40 located in the environmental chamber 10.

The MEC 40 is preferably made of a copper conductor or some suitable copper alloy or mixture thereof As suggested above, the number, shape, and dimensions of the MEC 40 and its conductors are not restricted and any change thereto should be understood to be well within the scope of the intended invention. The MEC 40 may consist of more than one conductor welded together, thus effectively integrating the heating and cooling functions. The first conductor delivering the heating (i.e., energy) with the second delivering the cooling medium (i.e., energy reduction). Subsequent conductors within the MEC 40 can be used as suggested above for other protective gases and the like. Inside the MEC 40, there is a holder 45 upon which a low thermal mass crucible 50 rests. This holder 45 supports the test sample during the operation of the UMSA system.

While the term "test sample" has been used for purposes of this description, it should be readily understood that "work piece" may be substituted for this term. Further, it should be recognized that a given test sample may include several work pieces such that the collective test sample is made of one or more materials. Still further, it should be understood that more than one work piece may be placed within the crucible 50 to create a testing sample that combines several different work pieces. The holder 45 provides for positioning and dynamic movement of the work piece(s) with respect to the MEC 40. An additional cooling system is incorporated into the holder 45. This allows for the cooling of the work piece(s) in a programmable manner including the temperature and the resulting structural gradient.

Located inside the crucible 50 is a test sample 55. The size and dimensions of the test sample 55 are not restricted and depend on the given application. Temperature sensors 60 are supported by an arm holder 42 and are positioned in arbitrary (e.g., x, y, z) directions with respect to the test sample 55. A data acquisition means 65 is connected to each of the temperature sensors 60 and to a computer 70. The computer 70 is also connected to the HFRI 15 and the two fluid cooling means 20. As mentioned, the computer 70 can be connected to a Local Area Network (LAN) or be a part of a multi-user system connected to the Internet from where it can be programmed, monitored, and controlled.

The computer 70 controls the UMSA apparatus, stores experimental data and analyzes the experimental data acquired during each step of a simulated thermal process. The operating parameters of the thermal process are either entered by an operator or copied from a storage memory, as a digitally duplicated, real industrial process file into the computer 70. The computer 70 controls the thermal process by engaging the HFRI 15, which delivers energy directly to the test sample 55 located inside the crucible via a high frequency Electromagnetic Field (EMF) generated by the MEC 40. The frequency of the EMF is selected and controlled by the computer 70 in such a way that eddy current (i.e., energy) is generated only in a very thin outside layer of the test sample and/or can penetrate its entire sample volume 55.

The EM field supplies the energy to heat the test sample 55 in a controlled manner during operation. While the test sample 55 is being heated, the sensors 60 collect the data from the test sample 55 and its surrounding environment. If the thermal process involves cooling, the computer 70 activates the cooling means 20 and circulates a cooling medium (e.g., liquids, gases, atomized liquids, . . . etc.) onto one or more of the conductors of the MEC 40 and the test sample 55. The computer 70 regulates the cooling rate in order to maintain the temperature of the testing sample 55 at the required level. The computer 70 also controls the temperature of the cooling medium of the MEC 40 to maintain it at a set requisite level. This operation is accomplished by way of the thermostatic bath. During the cooling of the MEC 40 and the test sample 55, the data acquisition means collects experimental data from the sensors 60 related to the test sample 55 and the environmental conditions. This experimental data is transmitted to the computer 70 where it is recorded and analyzed. The experimental data can be analyzed manually or the computer 70 can perform automated interactive analysis and display the summary results in a fully customized format. It should be readily understood that any software related to these computer functions is within the common knowledge of one skilled in the software art and further details of such software is not required within this description.

In operation of the UMSA apparatus, the method includes:

a) Heating a test sample with the heat source. Heating can be performed under a constant power mode. The constant power output is delivered to the test sample which is required if thermal analysis is to be performed. Heating can also be performed under a variable power mode. As such, the output power changes to maintain the required heating rate controlled by the TPC.

b) Cooling the test sample. Cooling can be performed with a constant power mode. This would involve cooling with a heat source such that the constant power output is delivered to the test sample. This option is required if thermal analysis is to be performed. Cooling can also be done with a variable power mode. Here, the output power changes to maintain the required cooling rate and is controlled by the TPC. Applying the cooling medium can further perform cooling. Here, the cooling medium flow is varied to maintain the required cooling rate or can be constant in order to perform thermal analysis.

c) Controlled quenching of the test sample. This is accomplished either by immersing the test sample in the quenching medium or by delivering the cooling medium through the MEC.

d) Controlled varying of the desired thermal gradient(s) in the work piece(s), and therefore in the resulting micro and macrostructure, during its solidification, quenching or heat treatment processes.

e) Isothermal Holding. Maintaining the required temperature of the test sample with a high degree of accuracy for a specified period of time does this. The operation can be done under constant and/or variable power conditions.

f) Surrounding the test sample surface(s) with protective gas(es) to protect the test sample from degradation during the operation of the UMSA apparatus. This can be accomplished via the MEC or in the environmental chamber.

g) Protecting and treating the test sample melt with powders and/or inert and/or reactive gases.

h) Superimposing the thermal process cycle(s) on the other testing conditions (i.e. a simultaneously performed high cycle fatigue test) during work piece(s) evaluation.

i) Monitoring and controlling the temperature/time data process parameters of the test sample during the heating, cooling, and isothermal holding steps.

j) Analyzing the physical characteristics of the test sample during and after the completion of the industrial process.

It should be understood that the preferred embodiments mentioned here are merely illustrative of the present invention. Numerous variations in design and use of the present invention may be contemplated in view of the following claims without straying from the intended scope and field of the invention herein disclosed.

What is claimed is:

1. A Universal Metallurgical Simulator and Analyzer (UMSA) apparatus for simulating and analyzing industrial processes, said UMSA apparatus comprising:

a holder for a test sample equipped with a cooling means;
a crucible;
at least one heat source for varying the temperature of said test sample in cooperation with said crucible;
at least one sensor;
a data acquisition means for recording data collected by said at least one sensor during said industrial processes;
a programmable controller for controlling at least one operating parameter of said industrial processes and for adjusting said at least one operating parameter based on said data collected by said data acquisition means;

at least one multifunctional excitation coil having a heating-cooling mode and capable of delivering protective gas to surfaces of said test sample;

said at least one heat source including at least one high frequency resonant inverter for delivering power to said at least one multifunctional excitation coil for generation of an electromagnetic field which heats said test sample, and said at least one high frequency resonant inverter controlling a variable penetration depth of said electromagnetic field within said test sample:

wherein said holder is coupled to said heat source, said at least one sensor is connected to said test sample and said data acquisition means, and said controller is coupled to said heat source and said data acquisition means.

2. The UMSA apparatus according to claim 1 further including said cooling means having a cooling medium for reducing the temperature of said test sample during said industrial processes wherein said cooling source is coupled to said holder and said controller.

3. The UMSA apparatus according to claim 1 further including a processing means for analyzing said data wherein said processing means is coupled to said data acquisition means.

4. The UMSA apparatus according to claim 3 wherein said at least one multifunctional excitation coil is a fused coil including at least two coil conductors.

5. The UMSA apparatus according to claim 4 wherein said at least two coil conductors contain a first conductor including a heating medium and a second conductor containing a cooling medium.

6. The UMSA apparatus according to claim 5 wherein said at least one multifunctional excitation coil includes a third conductor for delivering protective gas to a surface of said test sample.

7. The UMSA apparatus according to claim 6 wherein said programmable controller varies said power.

8. The UMSA apparatus according to claims 3 or 7 further including an environmental chamber for isolating said test sample from outside environmental conditions by enclosing at least said holder, said crucible, said at least one sensor, and said at least one multifunctional excitation coil.

9. A Universal Metallurgical Simulator and Analyzer (UMSA) apparatus for simulating and analyzing industrial thermal processes, said UMSA apparatus comprising:

an environmental chamber;

a crucible containing a test sample resting on a holder that is positioned inside at least one multifunctional excitation coil;

a plurality of sensors placed on and around said test sample for recording temperature versus time data;

at least one high frequency resonant inverter for supplying voltage and current to said at least one multifunctional excitation coil for generation of an electromagnetic field which heats said test sample, and said at least one high frequency resonant inverter controlling a variable penetration depth of said electromagnetic field within said test sample:

a two-fluid cooling system having a first fluid being applied to said test sample through an automated valve means and a second fluid being enclosed in a thermostatic bath circuit, said second fluid for cooling said at least one multifunctional excitation coil;

and a computer for controlling operating parameters of said industrial processes and for analyzing physical characteristics of said test sample during said industrial processes;

wherein at least said holder, said two-fluid cooling system, and said at least one multifunctional excitation coil are enclosed within said environmental chamber, and said computer is coupled to said plurality of sensors, said at least one high frequency resonant inverter, said automated valve means, and said thermostatic bath circuit.

10. The UMSA apparatus according to claim 9 wherein said crucible is composed of non-magnetic steel.

11. The UMSA apparatus according to claim 9 wherein said crucible is composed of a ceramic material.

12. The UMSA apparatus according to claims 10 or 11 wherein said crucible includes a lid, said lid and said holder being made from ceramic material to enable thermal analysis of said test sample.

13. The UMSA apparatus according to claim 9 wherein said crucible is coated.

14. A method for simulating and analyzing industrial processes using an UMSA apparatus, said method comprising:

heating a test sample with a heat source including at least one high frequency resonant inverter for supplying voltage and current to at least one multifunctional excitation coil that generates an electromagnetic field which heats said test sample, and said at least one high frequency resonant inverter controlling a variable penetration depth of said electromagnetic field within said test sample:

cooling said test sample;

quenching said test sample;

isothermally holding said test sample at a predetermined temperature for a specified period of time;

surrounding surfaces of said test sample with selected protective gas to protect said test sample from degradation during operation of said UMSA apparatus;

treating said test sample with protective media;

monitoring and controlling temperature/time process parameters of said test sample during said heating, said cooling, and said isothermally holding steps;

and analyzing physical characteristics of said test sample during and after completion of said industrial processes.

15. The method as claimed in claim 14 where said heating step is performed under a constant power mode such that constant power output is delivered to said test sample.

16. The method as claimed in claim 14 where said heating step is performed under a variable power mode such that output power delivered to said test sample changes to maintain a required heating rate controlled by a temperature process controller.

17. The method as claimed in claim 14 where said cooling step is performed under a constant power mode when thermal analysis is to be performed.

18. The method as claimed in claim 14 where said cooling step is performed under a variable power mode such that output power changes to maintain a required cooling rate controlled by a temperature process controller.

19. The method as claimed in claim 14 where said cooling step is performed by applying cooling medium such that flow of said cooling medium is varied to maintain a required cooling rate.

20. The method as claimed in claim 14 where said cooling step is performed by applying cooling medium such that flow of said cooling medium is constant in order to perform thermal analysis.

21. The method as claimed in claim 14 where said quenching step is performed by immersing said test sample in a quenching medium.

22. The method as claimed in claim 14 where said quenching step is performed by delivering a cooling medium through said at least one multifunctional excitation coil.

23. The method as claimed in claim 14 where said isothermally holding step is performed under constant power conditions.

24. The method as claimed in claim 14 where said isothermally holding step is performed under variable power conditions.

25. The method as claimed in claim 14 where said surrounding step is performed by way of an environmental chamber.

26. The method as claimed in claim 14 where said surrounding step is performed by way of said at least one multifunctional excitation coil.

27. The method as claimed in claim 14 where said protective media is chosen from the group consisting of powder, inert gas, and reactive gas.

28. The method as claimed in claim 14 further including, between said quenching step and said isothermally holding step, a step of varying thermal gradients within said test sample.

29. The method as claimed in claim 28 further including, between said treating step and said monitoring step, a step of superimposing a simultaneously performed test so as to evaluate other testing conditions during evaluation of said test sample.

* * * * *